US010325679B2

(12) United States Patent
MacDonald et al.

(10) Patent No.: US 10,325,679 B2
(45) Date of Patent: Jun. 18, 2019

(54) SYSTEMS AND METHODS FOR MEDICAL DATA COLLECTION AND DISPLAY

(75) Inventors: Hamish MacDonald, Dunedin (NZ); Atsushi Matsunaga, Hyogo (JP)

(73) Assignee: THE DIARY CORPORATION, Tucson, AZ (US)

( * ) Notice: Subject to any disclaimer, the term of this patent is extended or adjusted under 35 U.S.C. 154(b) by 347 days.

(21) Appl. No.: 13/822,628

(22) PCT Filed: Sep. 27, 2011

(86) PCT No.: PCT/IB2011/002907
§ 371 (c)(1),
(2), (4) Date: Mar. 12, 2013

(87) PCT Pub. No.: WO2012/042392
PCT Pub. Date: Apr. 5, 2012

(65) Prior Publication Data
US 2013/0191165 A1 Jul. 25, 2013

Related U.S. Application Data

(60) Provisional application No. 61/387,377, filed on Sep. 28, 2010, provisional application No. 61/417,835, filed on Nov. 29, 2010.

(51) Int. Cl.
*G16H 10/60* (2018.01)
*G16H 15/00* (2018.01)
*G16H 20/10* (2018.01)
(52) U.S. Cl.
CPC ............ *G16H 10/60* (2018.01); *G16H 15/00* (2018.01); *G16H 20/10* (2018.01)
(58) Field of Classification Search
CPC .... G06Q 50/22; G06Q 50/24; G06F 19/3418; G06F 19/3456; G06F 19/3412;
(Continued)

(56) References Cited

U.S. PATENT DOCUMENTS

2002/0082865 A1* 6/2002 Bianco et al. ............ 705/2
2003/0065537 A1  4/2003 Evans
(Continued)

FOREIGN PATENT DOCUMENTS

CA      1307855 C      9/1992
WO  WO 2012/090189 A1  7/2012

OTHER PUBLICATIONS

PCT, International Search Report and the Written Opinion, dated Apr. 13, 2012, for International Application No. PCT/IB11/02907.
(Continued)

*Primary Examiner* — Jonathan Durant
(74) *Attorney, Agent, or Firm* — Veros Legal Solutions, LLP

(57) ABSTRACT

A method and system for managing medical data is described. Medical data is stored in a database, where the medical data is supplied by both a patient and by other members of a care team authorized by the patient to provide medical data to the database, the other members of the care team including at least one of a physician, a pharmacist, other health professional and a family member of the patient. A computing device connected to a network provides at least some portions of the medical data (440, 450, 460, 470) supplied by the other members of the care team to the patient and provides at least some portions of the medical data (430) supplied by the patient to members of the care team that are authorized by the patient to receive at least some portions of the medical data, where the providing includes providing a plurality of graphic representations of medical data along a common timeline.

49 Claims, 7 Drawing Sheets

(58) Field of Classification Search
CPC ..... G06F 19/326; G06F 19/322; G16H 10/60; G16H 15/00; G16H 50/70; G16H 20/10; A61B 5/7435
See application file for complete search history.

(56) References Cited

U.S. PATENT DOCUMENTS

| | | |
|---|---|---|
| 2005/0182661 A1 | 8/2005 | Allard et al. |
| 2007/0016442 A1 | 1/2007 | Stroup |
| 2007/0106535 A1 | 5/2007 | Matsunaga |
| 2008/0127310 A1 | 5/2008 | Robbins et al. |
| 2008/0208631 A1 | 8/2008 | Morita et al. |
| 2008/0244453 A1 | 10/2008 | Cafer et al. |
| 2009/0043610 A1 | 2/2009 | Nadas et al. |
| 2009/0070136 A1* | 3/2009 | Morita et al. ............ 705/2 |
| 2009/0070146 A1 | 3/2009 | Haider et al. |
| 2010/0017754 A1 | 1/2010 | Cafer |
| 2010/0131293 A1 | 5/2010 | Linthicum et al. |
| 2010/0161353 A1 | 6/2010 | Mayaud |
| 2011/0074788 A1 | 3/2011 | Regan et al. |
| 2012/0131507 A1 | 5/2012 | Sparandara et al. |
| 2013/0191165 A1 | 7/2013 | MacDonald et al. |
| 2014/0143221 A1 | 5/2014 | Hoffmeister et al. |
| 2014/0180719 A1 | 6/2014 | Bell et al. |

OTHER PUBLICATIONS

PCT, International Preliminary Report on Patentability, dated Nov. 16, 2012, for International Application No. PCT/IB11/02907.
International Search Report for PCT/US2016/015392, dated Mar. 2, 2016, 4 pages.
Plaisant et al., "LifeLines: Using Visualization to Enhance Navigation and Analysis of Patient Records", HCIL Technical Report No. 98-08 (Oct. 1998).

* cited by examiner

SYSTEMS AND METHODS FOR MEDICAL DATA COLLECTION AND DISPLAY

CROSS-REFERENCE TO RELATED APPLICATIONS

This application claims the benefit of U.S. Provisional Application No. 61/387,377, filed Sep. 28, 2010, and entitled Systems and Methods for Medical Data Collection and Display, and U.S. Provisional Application No. 61/417,835, filed Nov. 29, 2010, and entitled Systems and Methods for Medical Data Collection and Display, both of which are incorporated by reference in their entirety.

BACKGROUND OF THE INVENTION

Field of the Invention

The field is medical records generally, and electronic medical records specifically, such as accessed via a web site.

Description of the Related Art

The field of medical records and electronic medical records is widely practiced. Unfortunately, it is also extremely fragmented, with patient data sourced from handwritten and typed notes, voice recordings, and a wide array of computer formats.

Physicians and other healthcare professionals are forced to read multiple pages of data, and mentally build a picture of what is happening, the order of events, and attempting to correlate drug or treatment changes with changes to the patient's physiological measurements or symptoms.

The present art does not provide a way for physicians to see, at a glance, a clear temporally correlated view of the relevant data for a patient.

Problems commonly experienced are: wasted time, greater expertise and training needed to read a patient chart, and errors including, too often, errors that cause serious injury or loss of life.

It has been shown by numerous Health Information Technology software applications and projects that simply coordinating or amalgamating information systems is not necessarily sufficient to improve the quality of information being accessed by clinicians and other healthcare professionals and users. The underlying problem is an entire care team for a patient needs access to a large amount of data but mostly need data to be summarized and presented in more useful ways. If the data is not appropriately summarized and easily understood, a healthcare professional will not be able to utilize it effectively.

SUMMARY

In one embodiment, there is a method for managing medical data comprising storing medical data in a database, wherein the medical data is supplied by both a patient and by other members of a care team authorized by the patient to provide medical data to the database, the other members of the care team comprising at least one of a physician, a pharmacist, other health professional, and a family member of the patient; providing, via a computing device connected to a network, at least some portions of the medical data supplied by the other members of the care team to the patient; and providing, via a computing device connected to a network, at least some portions of the medical data supplied by the patient to members of the care team that are authorized by the patient to receive the at least some portions of the medical data; wherein the providing comprises providing a plurality of graphic representations of medical data along a common timeline.

The method may additionally comprise automatically retrieving at least some of the medical data from one or more electronic medical records in the database. Providing at least some portions of the medical data may comprise transmitting a common web page containing a set of medical data to the patient and to the members of the care team.

In another embodiment, there is a computer implemented method for tracking medical data, comprising aggregating, via a computing device, medical data from disparate sources; structuring, via a computing device, the aggregated data into a database; inviting, via a computing device, one or more parties to provide medical data about a particular patient; identifying a source of each item of the provided data; structuring, via a computing device, the provided data into the database; and transmitting for display on an electronic display a plurality of data items with unique indicia for each data source so as to identify each unique data source.

One of the parties may be a medical professional. One of the parties may be a family member of the particular patient. The data about the particular patient may be patient owned. The invitation of the parties may be controlled by the particular patient. The health professional may be a pharmacist. The health professional may be a physician. The displaying may comprise applying a parameter to control a timescale for the plurality of data items. The medical data may pertain to a multiple medication protocol for the particular patient. The plurality of data items may be displayed in a single screen.

In another embodiment, there is a computer implemented method for tracking medical data, comprising aggregating, via a computing device, medical data from a plurality of sources; structuring, via a computing device, the aggregated data into a computer database; and transmitting for display, in a graphical format on an electronic display, the medical data in a single screen and oriented against a common timeline. The medical data may comprise data regarding a plurality of pharmaceuticals utilized by a particular patient, and the graphical format may indicate changes over time in the utilization of the pharmaceuticals by the particular patient, each one of the pharmaceuticals may be associated with a line against a common timeline indicative of a time period of utilizing the pharmaceutical, and at least some of the changes may be indicated by symbols associated with the lines.

One of the changes may be an increase or decrease of dosage or strength of one of the pharmaceuticals. The change of an increase or decrease of dosage or strength of one of the pharmaceuticals may be indicated on the display by a line with a step up for an increase in dosage or strength, or a line with a step down for a decrease in dosage or strength. The line may include associated text indicative of a first dosage or strength amount prior to the step and a second dosage or strength amount after the step.

One of the changes may be starting and/or stopping utilizing one of the pharmaceuticals. The change of starting and/or stopping utilization of one of the pharmaceuticals may be indicated on the display by a vertical line segment at a time corresponding to the starting and/or stopping.

One of the changes may be a replacement of one of the pharmaceuticals with one or more replacement pharmaceuticals. A replacement may be indicated on the display by a pair of spaced-apart vertical line segments at the timeframe of the replacement of the one of the pharmaceuticals. Each of the one or more other pharmaceuticals may have an associated line starting at the timeframe of the replacement, and each line may have associated text indicative of each of the other pharmaceuticals.

One of the changes may be splitting the dosage of one of the pharmaceuticals into a split dosage. The change of splitting the dosage may be indicated on the display by a symbol showing multiple doses starting at a timeframe when the dosage is split. The symbol may be associated with text indicative of the split dosage.

The method may additionally comprise adding a symbol to a line of any of the corresponding pharmaceuticals for which no changes are indicated for the timeframe displayed on the display. The method may additionally comprise associating text indicative of maintaining for the lines of the pharmaceuticals for which no changes are indicated.

One of the changes may be changing a frequency of taking one of the pharmaceuticals. Changing a frequency may be indicated on the display by a symbol showing a new frequency of taking one of the pharmaceuticals at a timeframe when the frequency changed. Text indicative of a new dosage after changing the frequency may be associated with the icon, and text indicative of a previous dosage may be associated with the line for the one of the pharmaceuticals prior to the timeframe when the frequency changed.

The method may additionally comprise associating text for each line indicative of the name of the pharmaceutical. Each line indicative of a pharmaceutical may have the same starting time, ending time and time scale.

In another embodiment, there is a system for tracking medical data, comprising a computing environment comprising a processor and a database in data communication with the processor, the computing environment configured to aggregate medical data from disparate sources, structure the aggregated data into the database, invite one or more members of a care team to view and provide medical data about a particular patient, identify a source of each item of the provided data, and provide for display on an electronic display a plurality of data items in a single screen with unique indicia for each data source.

The provided medical data may be entered automatically at a first time and entered manually at a second time. The processor may be a portion of a server, and the electronic display may be a portion of a client device. The computing environment may be connected to an electronic network.

In yet another embodiment, there is a system for tracking medical data, comprising a computing environment comprising a processor and a database in data communication with the processor, the computing environment configured to aggregate medical data from disparate sources, structure the aggregated data into the database, invite one or more members of a care team to view and provide medical data about a particular patient, wherein the care team includes the particular patient, family members, and healthcare professionals, and transmit for display to one or more members of the care team, in a graphical format on an electronic display, a plurality of medical data items in a single screen oriented against a common timeline. The medical data may comprise a plurality of pharmaceuticals utilized by a particular patient, and the graphical format may indicate changes over time in the utilization of the pharmaceuticals by the particular patient, each one of the pharmaceuticals may be associated with a line against a common timeline indicative of a time period of utilizing the pharmaceutical, and the changes may be indicated by symbols associated with the lines.

The provided medical data may be entered automatically at a first time and entered manually at a second time. The processor may be a portion of a server, and the electronic display may be a portion of a client device. The computing environment may be connected to an electronic network. The data about the particular patient may be patient owned. The invitation of the care team may be controlled by the particular patient. The healthcare professional may be a pharmacist.

One of the changes may be an increase or decrease of dosage of one of the pharmaceuticals. One of the changes may be starting and/or stopping utilizing one of the pharmaceuticals. One of the changes may be a replacement of one of the pharmaceuticals with one or more replacement pharmaceuticals. One of the changes may be splitting the dosage of one of the pharmaceuticals into a split dosage. An icon may be associated with a line of any of the pharmaceuticals for which no changes are indicated for the timeframe displayed on the display. One of the changes may be changing a frequency of utilizing one of the pharmaceuticals. Each line indicative of a pharmaceutical may have the same starting time, ending time and time scale.

The medical data about the particular patient may comprise laboratory results. The medical data about the particular patient may comprise background medical history.

DETAILED DESCRIPTION OF CERTAIN EMBODIMENTS

Introduction

Figure 1:
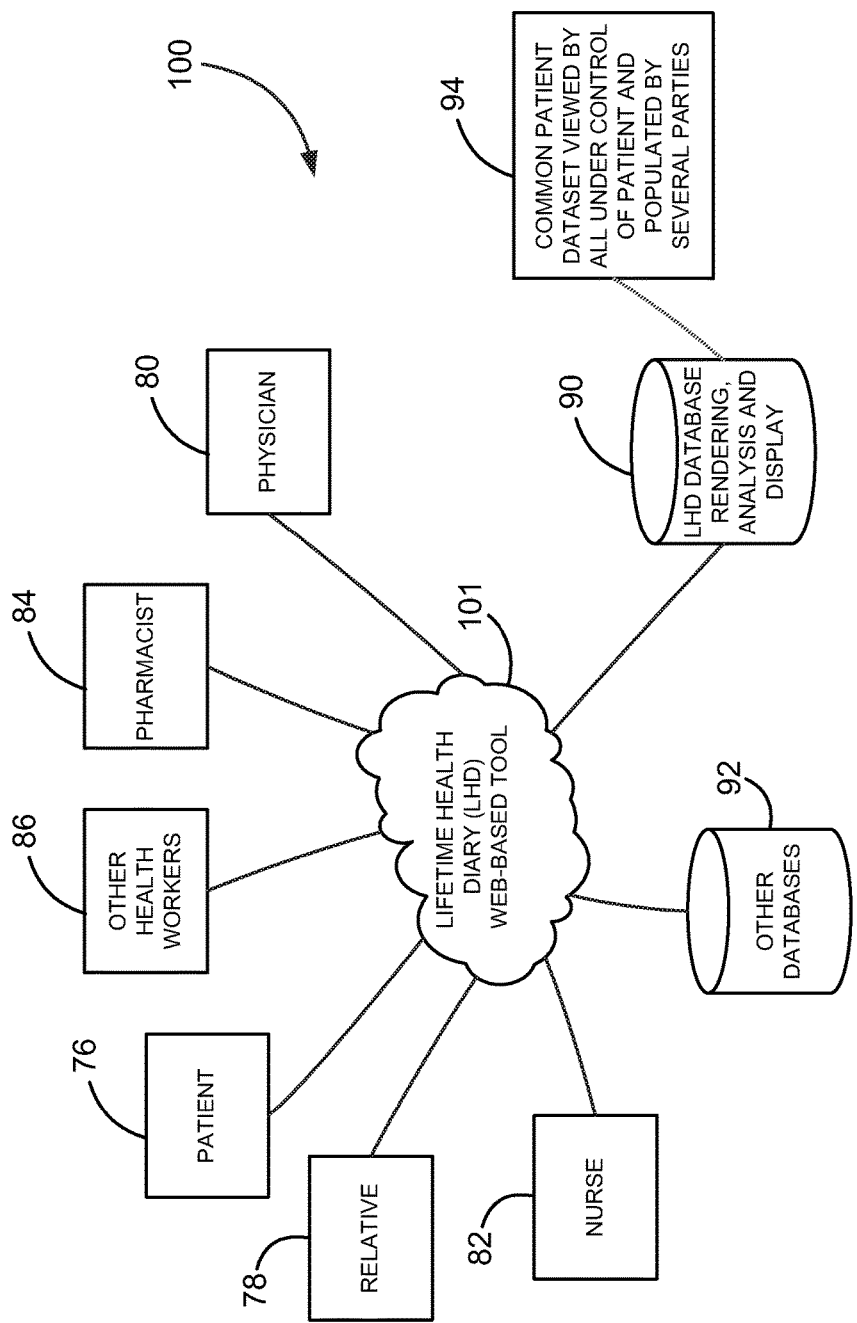
FIG. 1 is a diagram of an example of an embodiment of a system tool for creating maintaining and utilizing a Lifetime Health Diary.

The system and method described herein below can be implemented on various configurations of hardware and software. The system can be comprised of various modules, tools, and applications as discussed below. As can be appreciated by one of ordinary skill in the art, each of the modules may comprise various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system modules, tools, and applications may be written in any programming language such as, for example, C, C++, C#, BASIC, Visual Basic, Pascal, Ada, Java, HTML, XML, or FORTRAN, and executed on an operating system, such as variants of Windows, Macintosh, UNIX, Linux, VxWorks, or other operating system. C, C++, C#, BASIC, Visual Basic, Pascal, Ada, Java, HTML, XML and FORTRAN are industry standard programming languages for which many commercial compilers can be used to create executable code.

Definitions

The following provides a number of useful possible definitions of terms used in describing certain embodiments of the disclosed system and method.

Datum: a record of a drug or treatment, symptom, nutrition, lifestyle or lifestyle change, event, mental state, or physiological measurement or condition, comprising a time stamp, a symbol, icon or other means of denoting the event, plus optional fields such as a numerical value, regarding a patient condition or background information.

Data: A plurality of Datum

Data Source: any means of providing Data input, including but not limited to a healthcare professional, patient, software program, computer file or program, medical equipment, or sensor, etc., in any format including but not limited to handwritten notes, keyboard notes, audio or video recording, electronic file, etc.

Structuring: normalizing a Datum into a consistent and standardized record format Tracking: using time stamps or other fields in Structured Data to find, perform calculations on and based on, and graphically display correlations between Data.

Variable: in a clinical trial, treatment change, medication change, or other test or experiment, the Datum which is deliberately varied, while all other Datum are kept invariant (to the extent feasible).

Data Symbol: a graphical icon depicting a Datum, plus optional text or other depiction of additional information including but not limited to time stamp, numerical value, price, etc.

Time Line: a graphical depiction of a plurality of a particular kind of Data Symbols, sorted by their time stamps, or other field including but not limited to medication, or treatment or code number.

Infographic: a graphical or textual depiction of a table, chart, matrix, or other representation of Data Symbols corresponding to Data aggregated from a plurality of patients, sorted by time stamp, or other field including but not limited to age, gender, location, job, lifestyle choices, life events, underlying health conditions including pre-existing conditions, genetic identifier, symptoms, treatments, drugs, or healthcare provider, etc.

Rendering: displaying a plurality of Time Lines or Infographics, each having the same starting and ending time, and time scale.

Analyzing: a process of comprehending and considering the Data or Datum, either in isolation or in correlation or multiple correlations with another Datum or other Data, in order to better understand correlated or causal relationships.

Alert: An Alert is a real-time risk assessment, critical event, reminder, compliance indicator, general indicator, suggestion for medication and/or treatment, referral to a third party, or information pertinent to provision of healthcare. An Alert may include, but is not limited to, any graphical or textual content such as an icon, clock face, VU meter, barometer, thermometer, text, etc.

Message: A Message is the sending of an Alert via network by means including but not limited to, short message service (SMS), instant message, email, tweet, poke, text, automated or manual phone call, video, audio, any form of computer-mediated communication or any other format for sending information, etc.

Routing: Any means of determining appropriate care team members, the patient or other relevant third parties, based on factors including but not limited to, expertise, relationship to the patient, authentication, etc., and delivering a Message to said party or parties.

Network: A network may refer to a network or combination of networks spanning any geographical area, such as a local area network (LAN), wide area network (WAN), regional network, national network, and/or global network. The Internet is an example of a current global computer network. Those terms may refer to hardwire networks, wireless networks, or a combination of hardwire and wireless networks. Hardwire networks may include, for example, fiber optic lines, cable lines, ISDN lines, copper lines, etc. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

Website: A website may refer to one or more interrelated web page files and other files and programs on one or more web servers. The files and programs are accessible over a computer network, such as the Internet, by sending a hypertext transfer protocol (HTTP or HTTPS [S-HTTP]) request specifying a uniform resource locator (URL) that identifies the location of one of said web page files, wherein the files and programs are owned, managed or authorized by a single business entity. Such files and programs can include, for example, hypertext markup language (HTML) files, common gateway interface (CGI) files, and Java applications. The web page files preferably include a home page file that corresponds to a home page of the website. The home page can serve as a gateway or access point to the remaining files and programs contained within the website. In one embodiment, all of the files and programs are located under, and accessible within, the same network domain as the home page file. Alternatively, the files and programs can be located and accessible through several different network domains.

Web page or electronic page: A web page or electronic page may comprise that which is presented by a standard web browser in response to an HTTP request specifying the URL by which the web page file is identified. A web page can include, for example, text, images, sound, video, and animation.

Computer or computing device: A computer or computing device may be any processor controlled device, including terminal devices, such as personal computers, workstations, servers, clients, mini-computers, main-frame computers, laptop computers, a network of individual computers, mobile computers, palm-top computers, hand-held computers, set top boxes for a television, other types of web-enabled televisions, interactive kiosks, personal digital assistants (PDAs), interactive or web-enabled wireless communications devices, mobile web browsers, or a combination thereof. The computers may further possess one or more input devices such as a keyboard, mouse, touch pad, joystick, pen-input-pad, and the like. The computers may also possess an output device, such as a visual display and an audio output. One or more of these computing devices may form a computing environment.

These computers may be uni-processor or multi-processor machines. Additionally, these computers may include an addressable storage medium or computer accessible medium, such as random access memory (RAM), an electronically erasable programmable read-only memory (EEPROM), programmable read-only memory (PROM), erasable programmable read-only memory (EPROM), hard disks, floppy disks, laser disk players, digital video devices, compact disks, video tapes, audio tapes, magnetic recording tracks, electronic networks, and other techniques to transmit or store electronic content such as, by way of example, programs and data. In one embodiment, the computers are equipped with a network communication device such as a network interface card, a modem, or other network connection device suitable for connecting to the communication network such as the Internet. Furthermore, the computers execute an appropriate operating system such as Linux, UNIX, any of the versions of Microsoft Windows, Apple MacOS, IBM OS/2 or other operating system. The appropriate operating system may include a communications protocol implementation that handles all incoming and outgoing message traffic passed over the network. In other embodiments, while the operating system may differ depending on the type of computer, the operating system will continue to provide the appropriate communications protocols to establish communication links with the network.

The computers may contain program logic, or other substrate configuration representing data and instructions, which cause the computer to operate in a specific and predefined manner, as described herein. In one embodiment, the program logic may be implemented as one or more object frameworks or modules. These modules may be configured to reside on the addressable storage medium and configured to execute on one or more processors. The modules include, but are not limited to, software or hardware components that perform certain tasks. Thus, a module may include, by way of example, components, such as, software components, object-oriented software components, class components and task components, processes, functions, attributes, procedures, subroutines, segments of program code, drivers, firmware, microcode, circuitry, data, databases, data structures, tables, arrays, and variables.

The various components of the system may communicate with each other and other components comprising the respective computers through mechanisms such as, by way of example, interprocess communication, remote procedure call, distributed object interfaces, and other various program interfaces. Furthermore, the functionality provided for in the components, modules, and databases may be combined into fewer components, modules, or databases or further separated into additional components, modules, or databases. Additionally, the components, modules, and databases may be implemented to execute on one or more computers. In another embodiment, some of the components, modules, and databases may be implemented to execute on one or more computers external to the website. In this instance, the website includes program logic, which enables the website to communicate with the externally implemented components, modules, and databases to perform the functions as disclosed herein.

Description

Embodiments will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments. Furthermore, embodiments may include several novel features, no single one of which is solely responsible for its desirable attributes or which is essential to practicing the inventions herein described.

Some embodiments comprise systems and methods for providing relevant medical data on a chart so that a healthcare provider can quickly understand the history, the correlations of drugs, treatments, nutrition, lifestyle choices, patient physiology values (e.g., blood pressure), and symptoms, including changes to all of these. These systems and methods make it possible for healthcare providers as well as patients and other members of a care team with less training and expertise to competently read and analyze this data. Additionally, it minimizes the risk of errors.

Referring to FIG. 1, an embodiment of a system 100 includes a system tool 101 for creating, maintaining, and utilizing stored medical data pertaining to an individual. Such a collection of data may be referred to as a Lifetime Health Diary (LHD). Certain embodiments of the system 100 utilize a network as described in conjunction with FIG. 2A hereinbelow, or utilize a cloud, as described in conjunction with FIG. 2B hereinbelow. These embodiments may utilize a website having web pages to provide access to the tool for one or more of the following parties: a patient 76 (which may include a patient surrogate), a relative 78 (which may also include a family member, a neighbor, a guardian, and so forth), a physician (which may include a primary care physician and/or specialist physician(s)), a nurse 82, a pharmacist 84 (which may include a clinical pharmacist), and other healthcare workers 86 that are not previously enumerated. In certain embodiments, the system 100 includes a LHD database 90 that works with the tool 101 for rendering, analysis, and display of medical information such as a common patient dataset 94 viewed by all parties under control of the patient and populated by several parties.

Systems and methods for providing relevant medical data on a display in the manner as described herein have many advantages for healthcare providers and patients alike. For example, embodiments of the systems and the methods may provide one or more of the following features and benefits:

Collating data from disparate sources and creating a single database of this medical information allows for easy and rapid analysis of all relevant contextual data.

Converting data into a common structured format and a common data format.

Providing an easy to understand graphic analysis of a patient's overall health.

Providing an easy to understand graphic analysis of a patient's response to a possible drug or a change in their drug regime.

Providing an easy to understand graphic analysis indicating possible contra-indications and the likely source of adverse effects. This can include isolating pre-existing patient conditions and complaints from new side effects and/or treatment efficacy that can appear or disappear after starting a particular medication regime.

Alternative forms of health treatment can also be more easily compared to conventional treatment regimes, either for an individual patient, or on a population health basis.

Provides the ability to harness background health information from the patient, or from health professionals involved in patient care. This can be ordered via temporal correlation, enabling direct comparison and correlation with a particular medication regime.

Making it possible to discover relationships between drugs, medical and health data, patient data and professional health opinions of the data.

Reduces inappropriate prescribing.

Reduces medication errors and oversights.

Improves patient adherence, health outcomes and utilization.

Increases cost effectiveness of medication regimes.

Allows easy summation and comprehension of cost of various medication regimes.

Sends easy to comprehend medication regimes, in real-time, to appropriate parties These advantages over prior art medical data collection and display systems can be further enhanced because data can be received and displayed in a meaningful manner in real-time. The term "real time" is not used here to denote absolute simultaneous data collection, processing and display. Rather, real time means data collection, processing, and display are sufficiently near in time to the actual tracked events to allow treatment decisions to be made in a beneficial manner on an ongoing basis. This will typically allow for conventional time schedules for entering data into health care provider databases and the like, and a frequency of display based on a user's determination of what is suitable for the conditions being monitored. For example, real time may comprise daily, weekly, or monthly updates and/or display viewing depending on the conditions being monitored.

Such a real-time process means that more comprehensive, responsive, and/or cost efficient care (care optimization) can be provided by a health professional to a patient at the point-of-care. In many cases, this may obviate the need to send previously complex and difficult information to a specialist such as a pharmacologist to decipher and interpret, with the corresponding time and expense required.

Embodiments may comprise a health reconciliation tool for collating, analyzing and displaying patient health data from two or more sources at a single point of care.

Figure 2A:
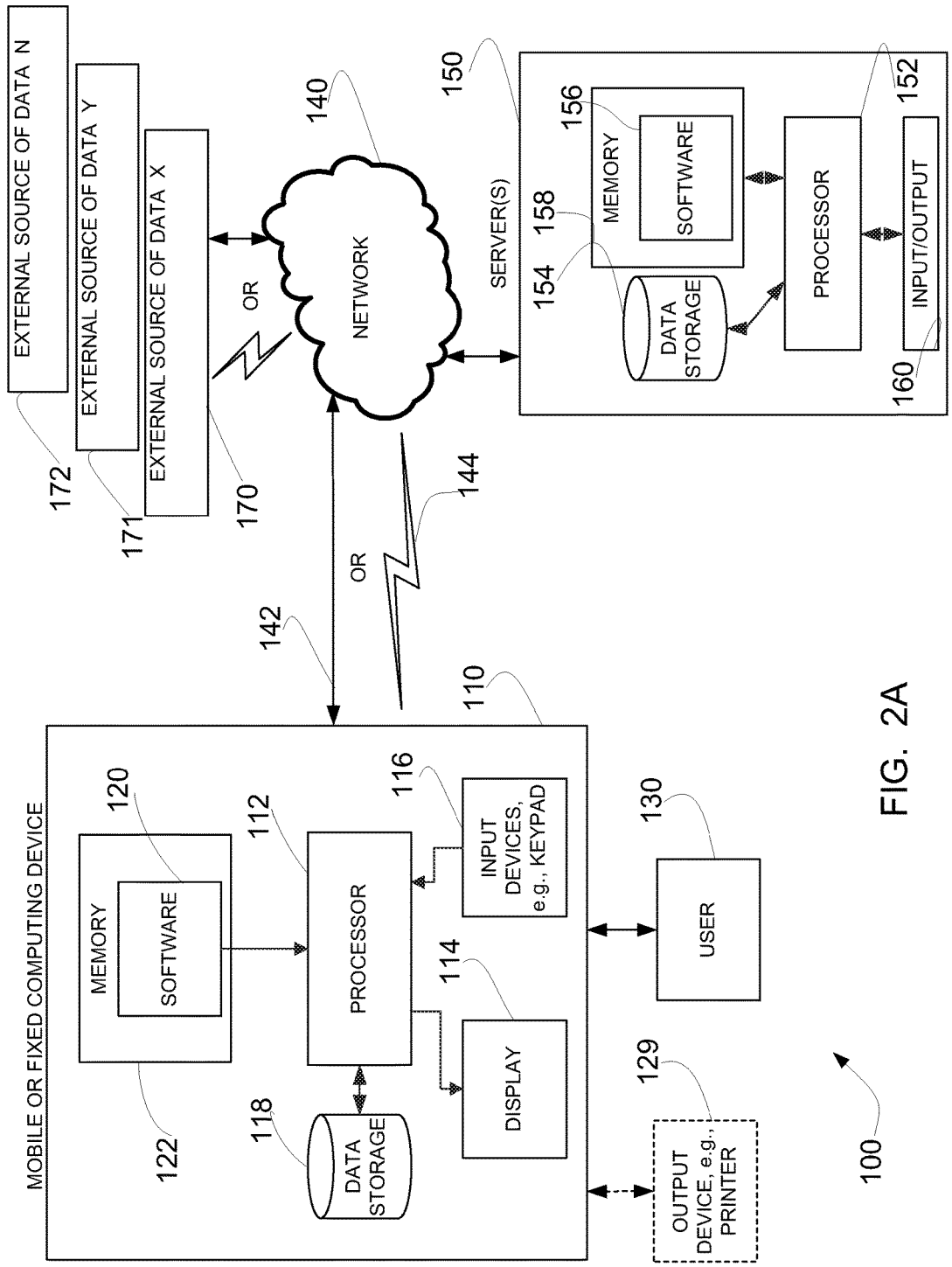
FIG. 2A is a diagram an example of an embodiment of a system configuration of the Lifetime Health Diary tool shown in FIG. 1.
Figure 2B:
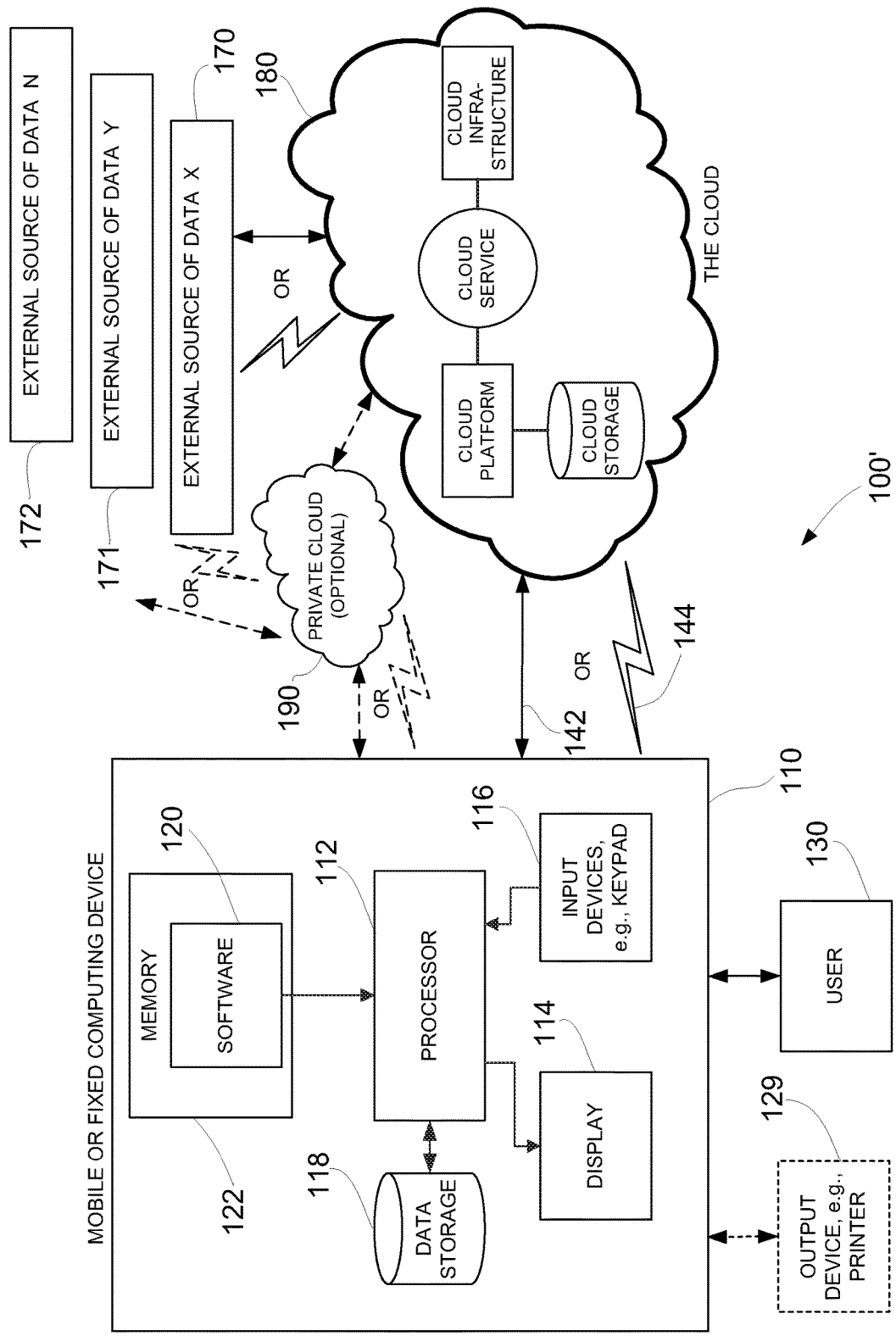
FIG. 2B is a diagram of an example of another embodiment of a system configuration of the Lifetime Health Diary tool shown in FIG. 1.

Certain embodiments are based on an example open system integrated architecture shown in FIG. 1, FIG. 2A and FIG. 2B. In FIGS. 2A and 2B, the example open system integrated architecture may be based on, for example, a user interface interacting with a local or remote data repository and a local or remote application running on a local or remote application server, such as an application server 150. FIGS. 2A and 2B are block diagrams of an example system 100 that may be used to implement certain systems and methods described herein. The functionality provided for in the components and modules of computing system 100 may be combined into fewer components and modules or further separated into additional components and modules. Various other types of electronic devices communicating in a networked environment may also be used.

Referring to FIG. 2A, an example configuration of components of an embodiment of the system 100 using a network will now be described. A mobile or fixed computing device 110 is operated by a user 130. There may be other mobile or fixed computing devices. The computing device 110 can be a handheld computing device or other portable computing device such as a Palm, Pocket personal computer (PC), Linux based handheld, PDA, smartphone such as an iPhone®, Tablet computer such as an iPad®, or PC having a display. In other embodiments, the computing device can be any form of Internet connected device, including but not limited to PCs, mobile devices, PDA, laptops, tablets, chips, keyboards, voice audio and video software, mouse, keypads, touch pads, track ball, microphones, videos, storage devices, network devices, databases, scanners, copiers, digital pens, image recognition software and device, screens and other forms of displays, netbooks and other forms of computer hardware. The computing device 110 in certain embodiments operates in a stand-alone (independent) manner. In other embodiments, the computing device 110 is in communication with one or more servers 150 via a network 140. The server(s) include one or processors 152, memory 158, data storage 154, system software 156 executed by the processor(s), and input or output devices 160. In certain embodiments, the data storage 154 stores one or more databases used by the system, such as the LHD database 90 (FIG. 1). The processor(s) 152 are in communication with the database(s) via a database interface, such as structured query language (SQL) or open database connectivity (ODBC). In certain embodiments, the data storage 154 is not included in server(s) 150, but is in data communication with the server(s) via the database interface. The connection from the computing device 110 to the network 140 can be a wireless or a satellite connection 144 or a wired or direct connection 142. In certain embodiments, the server(s) are part of a web site, such as on an intranet or the Internet.

When the computing device 110 is connected with the server(s) 150, the web site may optionally provide updates on new features. In another embodiment, the computing device runs only when connected to the server(s) 150.

The computing device 110 includes a processor 112, memory 122, a display 114, and one or more input devices 116. The processor 112 is in data communication with a data storage 118. In certain embodiments, the data storage 118 may store records of the user and/or other data or software. System software 120 is executed by the processor 112. The system software 120 may include an application graphical user interface (GUI). The application GUI can include a database interface to the data storage 118 of the computing device. In certain embodiments, the software is loaded from the data storage 118. In embodiments where the computing device 110 communicates with a web site, the processor utilizes browser software in place of or in addition to the software 120. The network browser may be, for example, Microsoft Internet Explorer®, Apple Safari®, Mozilla Firefox®, Google Chrome™, browsers from Opera Software™, and so forth. An optional output device 129, such as a printer is connected to the computing device 110.

External source of data X 170, external source of data Y 171 through external source of data N 172 communicate with wired or wireless connections to the network 140. External sources of data include but are not limited to clinics, hospitals, healthcare networks, insurance, pharmaceuticals, pharmacies, regional health boards, pharmacy benefit managers, population health entities, government and private institutions, paramedics, researchers, health coaches, pharmacologists, physicians and other health professionals, patient networks, educational institutes, employers, laboratories, traditional complementary and alternative medicine practitioners, pharma, clinical research organizations, remote medicine providers, allied health organizations, care givers and care giver organizations. The external source of data 170-172 can include host hardware, which in certain embodiments, uses either a completely redundant hardware infrastructure (e.g., parallel servers or load balancing swap servers) to deliver availability; or gain scalability for its data systems by implementing a multi-processor system for its active system and another multi-processor as a passive standby system. The external source of data 170-172 can also include operating systems (e.g., multiprocessing, multi-user, multitasking, and real-time) to provide a software platform on top of which the external entity's application programs can run and ensure that different programs and users running at the same time do not interfere with each other. The operating system is also responsible for security, such as ensuring that unauthorized users do not access the external source of data 170-172. The external source of data 170-172 can also include a database, such as a relational database from Oracle Corporation. A relational database securely consolidates information and ensures data quality, provides always-available access, scales to deliver the response times users demand, reduces downtime, automates administrative tasks and reduces operational costs through scalability. The external sources of data can push processed or unprocessed medical data which needs further processing to the server(s) 150 for processing of the medical data. The processed data is used to update the system LHD database.

Referring to FIG. 2B, an example configuration of components of an embodiment of the system 100 using a cloud computing architecture will now be described. The configuration of components in FIG. 2B is similar to that of FIG. 2A except that the network 140 and servers 150 of FIG. 2A are replace by the cloud 180 of FIG. 2B. An optional private cloud 190 can also be utilized. Cloud computing can include web-based tools or applications that users can access and use through a web browser as if it were a program installed locally on their own computer. In certain embodiments, the cloud 180 comprises various computers, servers and data storage devices that function to provide a cloud platform (e.g., a web front end), cloud service (e.g., a queue), cloud infrastructure, and cloud storage (e.g., database). A public/external cloud can be used with a private cloud in a hybrid cloud or a combined cloud environment in certain embodiments Presentation of Medical Information Typically, patient medical information is collected using XML data export files into a comma separated values (CSV) file, and then manually displayed in a spreadsheet. Different views of such a spreadsheet makes temporal correlation extremely challenging as the dates can be out of order if sorted by drug name, as are the dosages and any change in medication. On the other hand, other sort orders will mean that drug names are jumbled up, making the view even more confusing. The overall effect of the state of the art is to make decisions and judgment time consuming, non-intuitive, complicated, and usually requiring specific expertise.

Figure 3A:
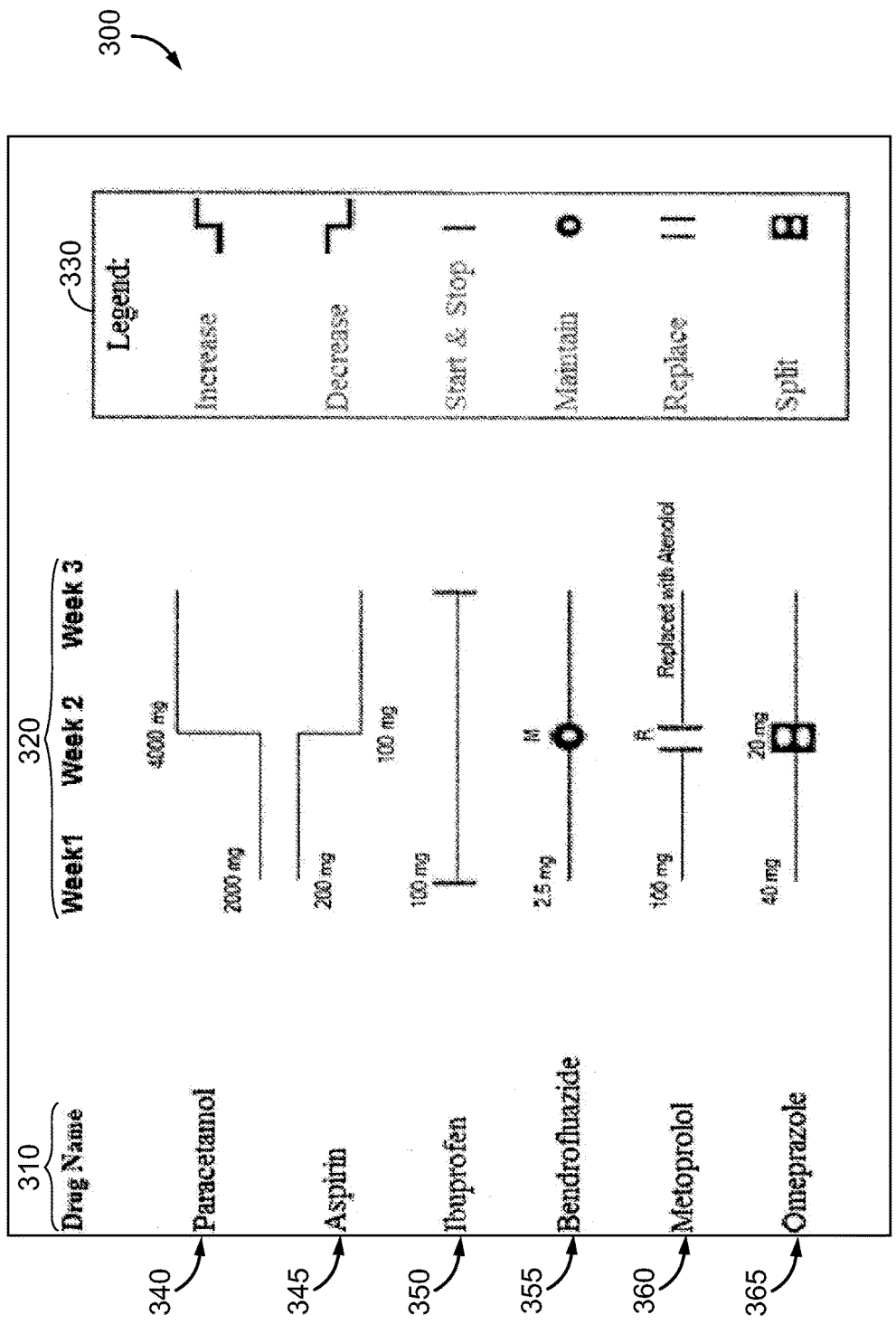
FIG. 3A is a display screen of an example of an embodiment of displaying multiple medications and changes over time for a particular patient.
Figure 3B:
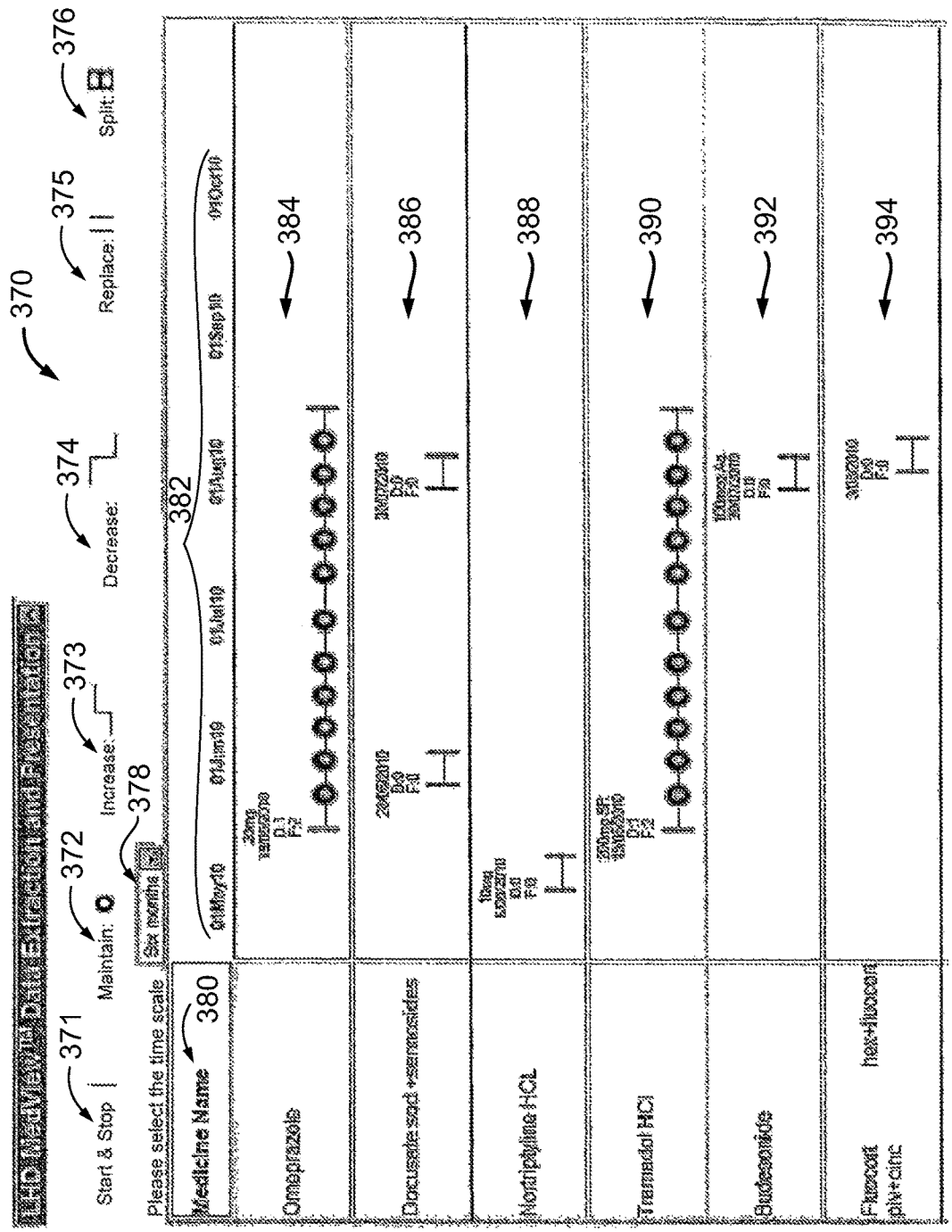
FIG. 3B is a display screen of an example of another embodiment of displaying multiple medications and changes over time for a particular patient.
Figure 4:
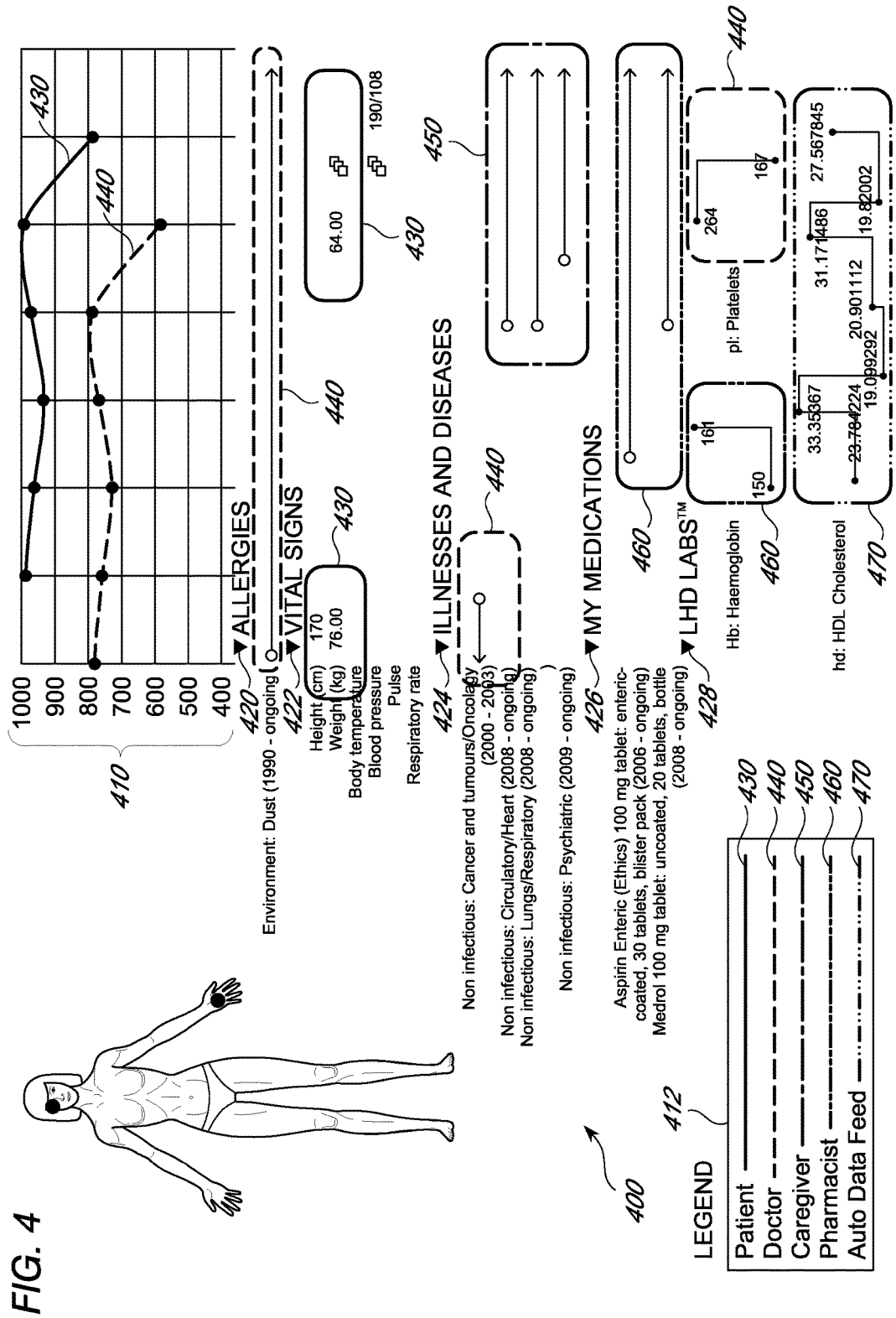
FIG. 4 is a display screen of an example embodiment of an amalgamation of medical information for a particular patient summarized into a single page screen.

By contrast, set forth below in FIGS. 3A, 3B, and 4 are examples of display formats that provide relevant data in a manner that is especially intuitive and helpful for all care team members.

In terms of data collection, data may be pulled as XML data export files (or any other suitable format) into the system that structures and displays them. Medical data may be imported from a variety of sources. These sources include systems that gather or store data about patients today such as paper records, voice recordings, computerized electronic medical records, or that might be developed in the future such as a nano-machine implanted in a patient's body and which uses a wireless communications method to periodically send physiology measurements. The data is structured so that it is put into a consistent computer record structure, with consistent fields, consistent units for values (e.g., grams), and so forth.

The data may be displayed using a consistent set of symbols to denote physiological measurements, drugs, dosages, starts and stops, and so forth. In certain embodiments, a series of vertically aligned horizontal lines are drawn, beginning at the start time (which may be the first time for which data is available, or any other time selected by the user), and ending at the end time (which may be the current time or optionally any prior time selected by the user). Each line contains data for one variable (e.g., a drug) or optionally, a set of related variables. A set of these lines is displayed on the screen or page (which may be the full set of all data for the patient or a subset chosen by the user). These lines may be synchronized, such that all have the same starting time, ending time, and time scale. This allows the user to see correlations and other relationships across data. In prior systems, these correlations and relationships were difficult or impossible to understand as they come from data that are provided by different sources and which is stored separately.

FIG. 3A shows a screen display 300 of possible modifications of medications (for example, increase, decrease, start, stop, maintain, replace, and dosage frequency). Each modification can be denoted visually on the display by a particular selected symbol. In the embodiment of FIG. 3A, a column for a drug name 310 is followed by a portion of the display 320 having a time period such as several days, weeks or months. In certain embodiments, the user interfaces with the system to select the desired time period to view. In the example shown in FIG. 3A, week 1, week 2 and week 3 are displayed with a horizontal line for the time period each of the drugs or pharmaceuticals is taken by the particular patient. The time scale is the same for each of the drugs. In this example, Paracetamol is shown in a row area 340 and has an associated symbol indicating an increase (step up) of the drug dosage and text associated with the horizontal line indicating a change of dosage from 2000 mg to 4000 mg at a timeframe during week 2. Aspirin is shown in a row area 345 and has an associated symbol indicating a decrease (step down) of the drug dosage and text associated with the horizontal line indicating a change of dosage from 200 mg to 100 mg at a timeframe during week 2. Ibuprofen is shown in a row area 350 and has vertical line symbols that show the drug use started at the beginning of week 1 and ended at the end of week 3. Bendrofluazide is shown in a row area 355 and has an associated symbol showing the drug use was maintained at a constant dosage and text associated with the horizontal line indicating a dosage of 2.5 mg to show the dosage throughout the three week period. Metoprolol is shown in a row area 360 and has an associated symbol of two short vertical lines to indicate a replacement of the drug to another drug, and text associated with the horizontal line indicating a replacement of Metroprolol to Atenolol at a timeframe during week 2. Text associated with the horizontal line can indicate the original dosage and/or the new dosage. Omeprazolel is shown in a row area 365 and has an associated symbol indicating a split of dosage or frequency of the drug to another dosage or frequency, and text associated with the horizontal line indicating a new dosage or frequency at a timeframe during week 2. Text associated with the horizontal line can indicate the original dosage or frequency. Of course, other symbols and/or text are contemplated in other embodiments along with other possible modifications of the patient medications.

FIG. 3B illustrates another embodiment of an example screen display 370 of medication data for a particular patient. A set of possible modification symbols are shown near the top of the screen display 370, and includes a start and stop symbol 371 (e.g., a short vertical line), a maintain symbol 372 (e.g., a shaded circle with the center not shaded), an increase symbol 373 (e.g., a step up), an decrease symbol 374 (e.g., a step down), a replace symbol 375 (e.g., two short vertical lines spaced apart), and a split symbol 376 (e.g., a shaded rectangle with two or more ovals to indicate a corresponding split dosage or frequency). A column 380 on the left side of the display screen 370 indicates a medicine name. A section 382 to the right of the medicine name shows a time period as selected by the user using a drop down selection menu 378 to select a time scale, which in this example is shown as six months from 01 May 10 to 01 Oct. 10. As in the example of FIG. 3A, the medicines for another particular patient are shown in row areas 384 to 394 in this example. Omeprazole is shown in row area 384 with a start symbol and text indicating a start date of 19/05/2010 and additional text indicating a drug dosage and frequency. Additional symbols indicating that the drug usage was maintained using the maintain symbol can be shown on the display at certain intervals, such as weekly or another time period. The display further shows that the usage of Omeprazole ended during the middle of August 2010 by use of the stop symbol. Docusate sod+sennosides is shown in row area 386 with a start symbol and text indicating a start date of 28/05/2010 and additional text that can indicate a drug dosage and frequency. The example display screen further shows that the usage of Docusate sod+sennosides ended in early June 2010, after a predetermined period of time such as a week or ten days, by use of the stop symbol. As second usage of Docusate sod+sennosides started on 30/07/2010 and ended in early August after the predetermined amount of time. Similarly to the above description, Nortriptyline HCL is shown as being used by the patient for a short time period in May 2010 at row area 388, Tramadol HCL is shown as being used and maintained by the patient from 19/05/2010 to the middle of August 2010 at row area 390, Budesonide is shown as being used by the patient for a short time period starting on 30/07/2010 at row area 392, and Fluocort is shown as being used by the patient for a short time period in August 2010 at row area 394. Of course, other symbols and/or text are contemplated in other embodiments along with other possible modifications of the patient medications.

Although not illustrated in FIGS. 3A and 3B, another piece of information that can be provided on these displays is a drug or treatment price next to each drug or treatment name. The displayed price may be per quarter, month, or any suitable time frame. A total cost of the treatment/drug regimen can also be displayed, assisting in comparisons of cost versus outcome for different treatment protocols.

In both FIGS. 3A and 3B, the display screen presents clear information about the medications the patient is taking as well as modifications to the medication regime. These screens illustrate a way to better assimilate and view and analyze complex drug regimes and their relative changes over time.

It may be noted that in these embodiments, the dates of starting a medication, and in some embodiments, stopping the medication are shown and correlated with one or more of the medication name, amount, and modification. This makes reading, comprehending, and judging the medication data significantly easier and quicker to undertake. This may allow not just specialists (such as rare and expensive clinical pharmacologists) to view and comprehend the data, but also physicians, clinicians, junior staff, researchers, caregivers, patients and their families and any other authorized and interested party.

Optionally, in some embodiments, the system and method can include the step of conducting one or more experiments or clinical trials, where one deliberately varies one value (e.g., a drug dosage) while controlling some or all others. The system and method show both the variable that is being changed, when it is being changed, and the consequences that are caused by that change (e.g., blood pressure). It also shows that other parameters are being kept invariant, or if the patient is non-compliant or for some reason something that was supposed to be invariant is changing, that is visible at a glance too.

Managing potential long-term medication risks for patients with complex medicine regimes and multiple co-morbidities is an ongoing challenge for health care teams. The system and method described herein enables care providers to quickly comprehend and optimize multiple-medication regimes in real-time at the point-of-care, also helping to prevent errors and enhancing oversight by the care team. Certain benefits include the following:

Identify clinical issues of a patient graphically, including drug to drug interactions, symptom-treatment reactions, and background longitudinal factors.

Encourage patient adherence and physician compliance, including reducing physician time required to view medication records.

Assist in management of high-risk patients, and improve patient outcomes.

Enable the most care- and cost-effective medications to be prescribed at the outset of treatment.

Demonstrate improved clinical outcomes from new therapies.

Enable comparative effectiveness studies in real time.

In some embodiments, a step of displaying a time line or other graphic, showing data including but not limited to patients' ages, genders, locations, jobs, lifestyle choices, life events, underlying health conditions including pre-existing conditions, genetic identifiers, symptoms, treatments, drugs, or other health-related variable is provided. This step can be useful in assessing medication or treatment success across the above-mentioned patient variables, discovering contraindications, or otherwise assessing medication efficacy and/or patient response.

FIG. 4 is an example screen display 400 illustrating a summary page of medical information for a particular patient, which may be plotted against patient background/symptom information using temporal correlation. Advantages of such a display include, without limitation, enriching clinical understanding of the patient history, reducing oversights and mistakes, and improving health outcomes and patient engagement. FIG. 4 includes an easy to understand graphic analysis of a patient's overall health as well as an easy to understand graphic analysis of a patient's response to a possible drug or change in their drug regime. Such a graphic analysis helps to identify possible contra-indications and the likely source of adverse effects.

Alternative forms of health treatment can be more easily compared to conventional treatment regimes, either for an individual patient as illustrated in FIG. 4 or on a population health basis (not shown). Other areas for optimization made possible by the system and method include, but are not limited to, optimization of supplements and nutrition, life events, lifestyle, traditional, complementary and alternative medicine, treatment regimes, patient inputs and feedback and other health professionals inputs and feedback.

Various data sets (e.g., lab tests, medications, vital signs, symptoms, and so forth) are rendered onto a single page summary for each particular patient. The data sets may be graphically summarized with data sourced from different parties shown in a different color or other indicia. The example screen display 400 has a graph 410 at the top of the summary page indicating a patient's severity of aggregate symptoms over time as considered by the patient (or surrogate) at curve 430 and as considered by the patient's physician or any clinician, health professional or caregiver at curve 440. The curve 430 and the curve 440 are representative of the severity of an aggregate patient symptom set, taken as a sum total of the number of symptoms, their location, their individual severity, and their length of time endured. A downwards line indicates that the aggregate symptom set is getting worse, and an upwards line indicates a return to no symptoms, for example, that can be indicated by a maximum score of 1000. In some embodiments, thousands of separate symptoms may be aggregated for these curves to produce a consolidated single health metric.

A legend area 412 indicates markings or indicia corresponding to a source of the medical information used in the summary display. For example, the legend shown in the screen display 400 includes indicia to indicate data sourced by a patient 430 in a vital signs area of the display screen, a doctor 440 in an allergies area, an illnesses and diseases area, and a lab results area, a caregiver 450 in the illnesses and diseases area, a pharmacist or automatic pharmacy data feed 460 in a my medications area and the lab results area, and an automatic data feed 470 (such as from a medical device that generates such a data feed) in the lab results area. Data can be graphed over a range of time periods (days/weeks/months/years) with detail available on a show/hide selector against each sub-heading. For example, show/hide selectors are shown for the sub-headings of allergies 420, vital signs 422, illnesses and diseases 424, my medications 426, and LHD lab results 428, each of which have an area of the screen display to graphically display medical information on a common time scale for the particular patient. Of course, other sub-headings and medical data can be displayed and other types of indicia can be used in the legend. In certain embodiments, a time scale is shown in the screen display. In a default or normal view of the screen display 400, the data associated with the sub-headings 420, 422, 424, 426 and 428, and with the graph 410 is aligned vertically according to date, such that data associated with a particular patient and corresponding to a particular date and time is vertically aligned. In certain embodiments, the time scale for a portion of the screen display 400, such as the graph portion 410, can have a different time scale than the rest of the display. In certain embodiments, the data sets associated with the sub-headings 420, 422, 424, 426 and 428 and/or the graph portion 410 can be moved backward or forward in time as a group of data, as desired by the user. In certain embodiments, a multiple medication and modification display such as shown in FIG. 3A or 3B is utilized in the my medications area of the display screen.

The system and method does not leave data and data sets in their original form, but instead, repurposes the data into the summary page, which the user can use as an aide for clinical decision-making, including bedside consultations. From the amalgamation of data on the summarised one page screen, for example, the user is also able to drill down through the system to the underlying medical data as needed, and all this can be displayed on a hand-held tablet computer or PC or mobile device.

As illustrated in FIG. 4, in advantageous embodiments, a variety of different types of medical data are displayed on a common timeline. The different types may include (1) vital signs such as height, weight, body temperature, blood pressure, and pulse rate, (2) the presence of illnesses and diseases, (3) medications the patient is taking, and (4) laboratory results such as derived from blood tests. It is preferable if all of this data is delivered as a single web page to the user. Even if the page is larger than a screen size, the user need only scroll to display all of the desired data, rather than having to navigate additional links to other web pages with the associated delay and difficulty of adjacent viewing. Preferably, all of the above mentioned categories of medical information are provided on the page, although in some cases, a subset of such data may be presented.

The system and method highlight issues which may not be easily visible in dispersed data sets. An easier-to-understand display assists with quicker and more comprehensive understanding of patient medication regimes, vitals, lab results, signs and symptoms, and other background health data.

An advantage of the system and method is that all members of a healthcare team (multi-disciplinary care team), including patient and caregivers (e.g., family and other primary caregivers), as well as automatic medical data feeds can all input their respective data and still have it collated and displayed on the same single summary page. This capability fundamentally alters the ability of all members of that care team to view the patient condition holistically, with reference to all data, across any time scale.

The system and method has the capability to act as a collaborative tool for the multi-disciplinary care team including enabling the patient or their family to be a part of the care team, alerting them to important risks and changes to the patient's situation.

Through patient consent, multiple members of the patient's care team may be invited to the patient record, allowing all authorized team members to view a part or all of the patient's medical status (depending on the level of authorization granted). This invitation functionality, combined with the ability of the system and method to render and display data inputs of all the care team members on a single page, significantly increases collaboration and effectiveness of the care team, both for individual decision-making and through collaboration.

The following examples describe how each member of the care team may use the system and method.

Pharmacists, nurses and healthcare workers collect data from the patient, and are able to see the treatment regimen recommended by the specialist (see below) with adjustments made by the physician. The system and method can also track the patient's progress once recommendations are implemented and provide the patient with more informed advice about their regimen.

Specialist physicians/clinical pharmacists can see the current regimen, plus any health background information collected, and make recommendations on new regimens for the physician. The system and method can also track the uptake of recommendations by the physician and monitor the patient's progress.

The Physician can see the recommended regimen, a repository of patient outcomes, and the medications the patient is picking up, as well as record any patient changes. If notes from other care providers are available, the system and method can draw upon their observations and experiences with the patient to fine tune care and respond to issues.

The patient and/or their primary caregivers at home (including community nurses and other health workers) are able to enter data as feedback. Access to the specialist's recommendations enables them to play a more informed and active role in their care.

The multi-disciplinary care team is provided with a seamless view of patient regimens as well as outcomes and consequences of the regimen. Time is saved, mistakes and assumptions may be avoided, and collaboration amongst the entire care team (including the patient) is made easier.

A healthcare provider may expect the advantages of better individual health outcomes (better control of the condition, less adverse drug events, less emergency room visits, fewer hospitalizations and less doctor visits), with better population health visibility regarding outcomes of treatment.

Figure 5:
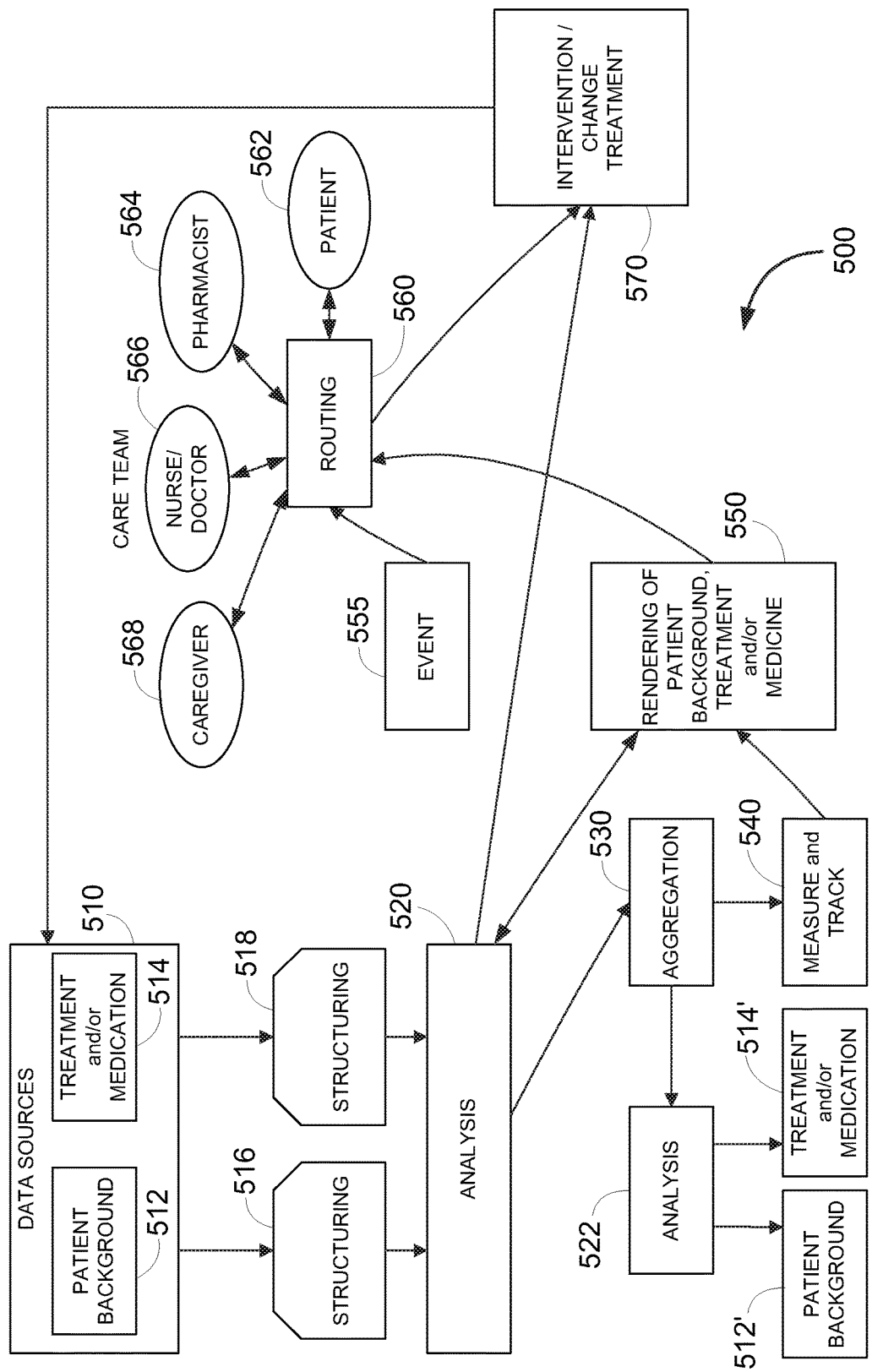
FIG. 5 is a diagram of an example of an embodiment of processing medical information for a particular patient.

Referring now to FIG. 5, an example of an embodiment a process 500 of processing medical information for a particular patient will be described. Data sources 510, such as described above, provide medical information such as patient background information 512 and treatment and/or medication information 514 along with any other previously mentioned medical information for a particular patient. In one embodiment, the patient background information is structured by a structuring process 516 and the treatment and/or medication information is structured by a structuring process 518. In other embodiments, other arrangements may be used for structuring certain medical information. After the medical information is structured, including normalizing the information into a consistent and standardized record format, an analysis process 520 performs analysis by processing the complex relationships between data. This analysis of the patient background, treatment and/or medication information and other patient data can be rendered on the screen visually at a process 550 including but not limited to the form of color, highlighter, arrows, or indicators. The analysis can also be used by the system and method to suggest that a healthcare professional make changes to a drug or treatment, or to a clinical trial or experiment. If desired, the analysis process 520 can also be used to determine if there is a risk or critical event, or if a suggestion for medication and/or treatment or referral to a third party is appropriate. Means of determination include heuristics or algorithms that consider the patient's data. The output of this process can include an alert to be sent as a message.

The output of the analysis process 520 can be sent to the rendering process and/or to an intervention or change treatment state 570. Some embodiments may determine the appropriate people to receive each message based on their expertise, relationship to the patient, authentication and other relevant information at a routing process 560 which receives input from the rendering process 550, or event information 555. The routing process can ensure that messages are sent to all appropriate recipients but not to anyone else. The potential recipient include, but are not limited to, a patient 562, a pharmacist 564, a nurse and/or doctor 566, and a caregiver 568, which are all part of the multi-disciplinary care team. The routing process 560 can also receives information from any member of the multi-disciplinary care team and route the information to the intervention or change treatment state 570. Any intervention or changed intervention information can be sent as a new data source to data sources 510.

The output of the analysis process 520 can also be sent to an aggregation process 530. The aggregation process 530 includes sorting data from disparate sources by time stamp, or other field including but not limited to age, gender, location, job, lifestyle choices, life events, underlying health conditions including pre-existing conditions, genetic identifier, symptoms, treatments, drugs, or healthcare provider. The aggregating may be expanded to include an optional step of aggregating data corresponding to a plurality of patients whose care is provided by a particular health care professional, health care facility, region, nation, and/or any particular form of treatment provision across a population or individually targeted subsets of a population. The output of the aggregation process 530 is sent to an analysis process 522, which can enable the user to correlate medications and treatments prescribed and performed to determine a number of factors regarding these care providers, including over- or under-prescription of medication, treatment effectiveness, superior or inferior diagnosing of particular symptoms or diseases, recognition of contraindications, and so forth. This may be useful to determine a healthcare provider's particular areas of expertise, and/or the effectiveness of a particular treatment regimen, and/or areas where additional training or education is needed. Results of the analysis can be stored in the LHD database as patient background data 512', treatment and/or medication data 514', or other data.

The output of the aggregation process 530 is also sent to a measure and track process 540 to track, monitor and measure outcomes for medications or treatments as prescribed by a particular health care professional, health care facility, region, nation, and/or any particular form of treatment provision across a population, individually targeted subsets of a population, or a particular patient. The output of the measure and track process 540 can be used as an input to the rendering process 550, described above.

The system and method captures multiple types of data from different types of fields, captured from various different sources. The system and method repurposes any kind of medical data from any kind of source to be on the graphical summary pages, such as shown in FIG. 4, to be more useful and meaningful for the care team, including patient and family caregivers.

The following data fields in Table 1 show several examples of data capture source. These are just illustrative; the data source in the right column could be any combination of the various data sources listed. An additional source that could be used for any of the data fields is an electronic medical record (EMR). The data extract from a data feed from an EMR, Pharmacy Management Software (PMS) or Lab Feed can be HL7-compliant XML data. The system and method effectively standardizes all the disparate data into a standard, consistent, easy-to-understand single format for all care team members to share and gain insight from.

TABLE 1

| Data Field | Captured By |
| --- | --- |
| Vital signs | Robot |
| Medications dispensed | Nurse or Pharmacist |
| Medications taken | Caregiver, Patient, Family |
| Test and Labs | Nurse or Physician |
| Immunizations | Nurse, Physician, or Lab Web Services |
| Signs | Nurse, Physician, or PMS Web Services |
| Symptoms | Caregiver, Patient, Family |
| Life events/Lifestyle | Caregiver, Patient, Family |

The overall effect of the system and method is to reduce oversights, omission and mistakes, as well as allow a health professional to more comprehensively diagnose, and in less time.

CONCLUSION

Various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer implemented method for dynamically tracking medical data and generating new displays in a computing environment having a network, the method comprises:
    a) aggregating, via a computing device in data communication with the network, medical data from a plurality of sources comprising separately stored medical records;
    b) structuring, via a computing device in data communication with the network, the aggregated data into a computer database;
    c) inviting, through patient consent, via a network in communication with the computing device, patient-selected one or more members of a care team to view and/or write medical data and background data about a particular patient, wherein the care team includes the particular patient, family members, and healthcare professionals, and wherein each of the care team members may thereby have one or more of view authorization, write authorization or no authorization, wherein the patient background data comprises at least one of nutrition, locations, jobs, lifestyle choices and life events;
    d) providing an interactive graphical user interface on a computing device corresponding with the patient and each of the care team members having view authorization and/or write authorization;
    e) transmitting for display on the interactive graphical user interface to each one of the one or more members of the care team authorized to view medical data and background data about the particular patient, on an electronic display of a computing device, a plurality of medical data items and background data items as part of a single webpage, wherein the webpage is configured to orient the medical data items and the background data items against a common timeline, wherein the webpage includes a user control included in the interactive graphical user interface, wherein the user control does not include network navigation links to other medical data items about the particular patient, wherein the user control facilitates a care team member having view authorization to select a start time and/or select an end time for the common timeline, and wherein the user control facilitates a care team member having view authorization to select which medical data items are shown or hidden from display against the common timeline, wherein the medical data comprises a plurality of medical data items regarding a plurality of pharmaceuticals utilized by the particular patient, and wherein the interactive graphical user interface indicates changes over time in the utilization of the pharmaceuticals by the particular patient, wherein the transmitting for display includes iteratively performing for each one of the pharmaceuticals utilized by the particular patient:
  i) automatically displaying a separate line in parallel to the common timeline and having a common timescale indicative of a time period of utilizing a particular pharmaceutical, wherein the changes are indicated by symbols inline with the lines, wherein each symbol corresponds to a particular timeframe of the change on the line, wherein the changes include an increase or decrease of dosage or strength of one of the pharmaceuticals, a replacement of one of the pharmaceuticals with one or more replacement pharmaceuticals, and changing a frequency of taking one of the pharmaceuticals, wherein the changes in the utilization of the pharmaceuticals include a plurality of types of changes, each type of change indicated by a unique symbol, wherein each of the unique symbol (s) visually displayed on the separate line are displayed directly as a result of a particular change regarding the pharmaceutical,
  ii) until all of the plurality of pharmaceuticals utilized by a particular patient are displayed;
f) constantly monitoring any new medical data to detect new pharmaceutical related data; and
g) if new pharmaceutical related data is detected, generating a new display screen including alerting a computing device to automatically extend the timeline if the medical data corresponds to a timeframe not displayed and further:
  i) adding any appropriate inline symbols to an existing line if the new data corresponds to an existing pharmaceutical utilized by the particular patient, or
  ii) generating a new line and any appropriate inline symbols if the new data corresponds to a new pharmaceutical utilized by the particular patient.

2. The method of claim 1, wherein the change of an increase or decrease of dosage or strength of one of the pharmaceuticals is indicated on the display by a line with a step up for an increase in dosage or strength, or a line with a step down for a decrease in dosage or strength.

3. The method of claim 2, wherein the line includes associated text indicative of a first dosage or strength amount prior to the step and a second dosage or strength amount after the step.

4. The method of claim 1; wherein one of the changes is starting and/or stopping utilizing one of the pharmaceuticals.

5. The method of claim 4, wherein the change of starting and/or stopping utilization of one of the pharmaceuticals is indicated on the display by a vertical line segment at a time corresponding to the starting and/or stopping.

6. The method of claim 1, wherein a replacement is indicated on the display by a pair of spaced-apart vertical line segments at the timeframe of the replacement of the one of the pharmaceuticals.

7. The method of claim 6, wherein each of the one or more other pharmaceuticals has an associated line starting at the timeframe of the replacement, and wherein each line has associated text indicative of each of the other pharmaceuticals.

8. The method of claim 1, wherein one of the changes is splitting the dosage of one of the pharmaceuticals into a split dosage.

9. The method of claim 8, wherein the change of splitting the dosage is indicated on the display by a symbol showing multiple doses starting at a timeframe when the dosage is split.

10. The method of claim 9, wherein the symbol is associated with text indicative of the split dosage.

11. The method of claim 1, additionally comprising adding a symbol to a line of any of the corresponding pharmaceuticals for which no changes are indicated for the timeframe displayed on the display.

12. The method of claim 11, additionally comprising associating text indicative of maintaining for the lines of the pharmaceuticals for which no changes are indicated.

13. The method of claim 1, wherein changing a frequency is indicated on the display by a symbol showing a new frequency of taking one of the pharmaceuticals at a timeframe when the frequency changed.

14. The method of claim 13, wherein text indicative of a new dosage after changing the frequency is associated with the icon, and text indicative of a previous dosage is associated with the line for the one of the pharmaceuticals prior to the timeframe when the frequency changed.

15. The method of claim 1, additionally comprising associating text for each line indicative of the name of the pharmaceutical.

16. The method of claim 1, wherein each line indicative of a pharmaceutical has the same starting time, ending time and time scale.

17. The method of claim 1, wherein one of the plurality of sources comprises medical equipment or a sensor.

18. The method of claim 1, wherein the medical data further comprises data items corresponding to the particular patient with unique indicia for each data source so as to identify each unique data source of the plurality of sources.

19. The method of claim 1, additionally comprising providing, via a computing device connected to a network in a computing environment, a web page having at least some portions of medical data supplied by members of a care team to the patient.

20. The method of claim 1, additionally comprising receiving user input in the interactive graphical-user interface at a control configured to change a time scale and/or scroll to a different portion of the graphical format of the patient medical data and background data.

21. The method of claim 1, additionally comprising constantly monitoring a graphical interface to detect a change in time scale and/or a change in position of at least a portion of graphic representations displayed to the user.

22. The method of claim 1, additionally comprising:
  generating an alert signal upon certain conditions being met using at least the patient medical data and background data;
  generating a message corresponding with the alert signal;
  based on the alert signal, triggering a determination of care team members having view authorization;
  transmitting the message via the network to the determined care team members having view authorization;
  constantly automatically monitoring for an input received via the network for a response to the message;
  based on the response, triggering a determination of care team members having write authorization;
  receiving an intervention or change in treatment from a computing device corresponding to a care team member having write authorization.

23. The method of claim 1, additionally comprising:
generating an alert signal upon certain conditions being met using at least the patient medical data and background data, wherein the alert signal is distributed to those authorized by the patient to receive the alert signal and to those authorized by the patient to provide an input in response to the alert signal; and
constantly automatically monitoring for an input received from at least one care team member having write authorization in response to the alert signal;
wherein the alert signal indicates that a healthcare professional is to make changes to a drug or treatment protocol, or to a clinical trial or experiment.

24. The method of claim 1, additionally comprising:
generating an alert signal upon certain conditions being met using at least the patient medical data and background data, wherein the alert signal is distributed to those authorized by the patient to receive the alert signal and to those authorized by the patient to provide an input in response to the alert signal; and
constantly automatically monitoring for an input received from at least one care team member having write authorization in response to the alert signal;
wherein the alert signal indicates that there is a risk or critical event for the particular patient, and that a healthcare professional is to suggest or refer the particular patient to a particular care team member or to a third party as appropriate.

25. The method of claim 1, wherein each item/type of the patient medical data and the patient background data is associated with a separate line displayed in parallel along the common timeline.

26. The method of claim 1, wherein the patient background data is received from a family member or caregiver for the particular patient.

27. The method of claim 1, wherein the transmitting for display on the interactive graphical user interface includes determining a subset of the patient's care team members that can view the medical data and background about the patient based on the member's view authorization and at least one of the member's expertise and relationship to the patient.

28. The method of claim 22, wherein determination of care team members having view authorization is based on a care team member having view authorization and one or more of a member's expertise and relationship to the patient.

29. The method of claim 22, wherein determination of care team members having write authorization is based on a care team member having write authorization and one or more of a member's expertise and relationship to the patient.

30. A system for tracking and processing medical data, comprising:
a computing environment comprising a processor, a network m data communication with the processor and a database in data communication with the processor, the computing environment configured to:
aggregate medical data from disparate sources; structure the aggregated data into the database,
invite, through patient consent, patient-selected one or more members of a care team to view and/or write medical data and background data about a particular patient, wherein the care team includes the particular patient, family members, and healthcare professionals, and wherein each of the care team members may thereby have one or more of view authorization, write authorization or no authorization, wherein the patient background data comprises at least one of nutrition, locations, jobs, lifestyle choices and life events;
provide an interactive graphical user interface on a computing device corresponding with the particular patient and each of the care team members having view authorization and/or write authorization; and
transmit for display on the interactive graphical user interface to each one of the one or more members of the care team authorized to view medical data and background data about the particular patient, on an electronic display of a computing device, a plurality of medical data items and background data items as part of a single webpage, wherein the webpage is configured to orient the medical data items and the background data items against a common timeline, wherein the webpage includes a user control included in the interactive graphical user interface, wherein the user control does not include network navigation links to other medical data items about the particular patient, wherein the user control facilitates a care team member having view authorization to select a start time and/or select an end time for the common timeline, and wherein the user control facilitates a care team member having view authorization to select which medical data items are shown or hidden from display against the common timeline, wherein the medical data comprises a plurality of medical data items regarding a plurality of pharmaceuticals utilized by the particular patient, and wherein the interactive graphical user interface indicates changes over time in the utilization of the pharmaceuticals by the particular patient for display on the interactive graphical user interface to each of the one or more members of the care team authorized to view medical data about the particular patient,
wherein the computing environment being configured to transmit for display includes an iterative execution for each one of the pharmaceuticals utilized by the particular patient to:
display a separate line in parallel to the common timeline and having a common timescale indicative of a time period of the particular patient utilizing a particular pharmaceutical, wherein the changes are indicated by symbols inline with the lines, wherein each symbol corresponds to a particular timeframe of the change on the line, wherein the changes include an increase or decrease of dosage or strength of one of the pharmaceuticals, a replacement of one of the pharmaceuticals with one or more replacement pharmaceuticals, and changing a frequency of taking one of the pharmaceuticals, wherein the changes in the utilization of the pharmaceuticals include a plurality of types of changes, each type of change indicated by a unique symbol, wherein each of the unique symbol(s) visually displayed on the separate line are displayed directly as a result of a particular change regarding the pharmaceutical,
until all of the plurality of pharmaceuticals utilized by a particular patient are displayed,
constantly monitor any new medical data to detect new pharmaceutical related data, and
if new pharmaceutical related data is detected, generate a new display screen including alerting a computing device to automatically extend the timeline if the medical data corresponds to a timeframe not displayed and to further:
add any appropriate symbols to an existing line if the new data corresponds to an existing pharmaceutical utilized by the particular patient, or
generate a new line and any appropriate inline symbols if the new data corresponds to a new pharmaceutical utilized by the particular patient.

31. The system of claim 30, wherein the provided medical data is entered automatically at a first time and entered manually at a second time.

32. The system of claim 30, wherein the processor is a portion of a server, and the electronic display is a portion of a client device.

33. The system of claim 30, wherein the computing environment is connected to an electronic network.

34. The system of claim 30, wherein the data about the particular patient is patient owned.

35. The system of claim 30, wherein the invitation of each of the care team members is controlled by the particular patient.

36. The system of claim 30, wherein one of the healthcare professionals is a pharmacist.

37. The system of claim 30, wherein one of the changes is an increase or decrease of dosage of one of the pharmaceuticals.

38. The system of claim 30, wherein one of the changes is starting and/or stopping utilizing one of the pharmaceuticals.

39. The system of claim 30, wherein one of the changes is splitting the dosage of one of the pharmaceuticals into a split dosage.

40. The system of claim 30, wherein an icon is associated with a line of any of the pharmaceuticals for which no changes are indicated for the timeframe displayed on the display.

41. The system of claim 30, wherein each line indicative of a pharmaceutical has the same starting time, ending time and time scale.

42. The system of claim 30, wherein the medical data about the particular patient comprises laboratory results.

43. The system of claim 30, wherein the medical data about the particular patient comprises background medical history.

44. The system of claim 30, wherein one of the disparate sources comprises medical equipment or a sensor.

45. The system of claim 30, wherein the medical data further comprises data items corresponding to the particular patient with unique indicia for each data source so as to identify each unique data source of the disparate sources.

46. The system of claim 30, wherein the computing environment is additionally configured to provide a web page having at least some portions of medical data supplied by members of the care team to the patient.

47. The system of claim 30, wherein the computing environment is additionally configured to:
generate an alert signal upon certain conditions being met using at least the patient medical data and background data;
generate a message corresponding with the alert signal;
based on the alert signal, trigger a determination of care team members having view authorization;
transmit the message via the network to the determined care team members having view authorization;
constantly automatically monitor for an input received via the network for a response to the message;
based on the response, trigger a determination of care team members having write authorization;
receive an intervention or change in treatment from a computing device remote from the processor corresponding to a care team member having write authorization.

48. The system of claim 47, wherein determination of care team members having view and/or write authorization is based on a care team member having view and/or write authorization and one or more of a member's expertise and relationship to the patient.

49. The system of claim 30, wherein the interactive graphical user interface further includes a user control to facilitate a care team member having view authorization to select one or more particular categories of medical data and background data to be viewed.

* * * * *